(12) United States Patent
Sarkar et al.

(10) Patent No.: US 9,936,890 B2
(45) Date of Patent: Apr. 10, 2018

(54) METHOD AND APPARATUS FOR ADJUSTING A THRESHOLD DURING ATRIAL ARRHYTHMIA EPISODE DETECTION IN AN IMPLANTABLE MEDICAL DEVICE

(71) Applicant: Medtronic, Inc., Minneapolis, MN (US)

(72) Inventors: Shantanu Sarkar, Roseville, MN (US); Daniel L Hansen, Castle Rock, CO (US); Grant A Neitzell, Seattle, WA (US); Jerry D Reiland, Coon Rapids, MN (US); Ryan Wyszynski, Oak Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 243 days.

(21) Appl. No.: 14/926,419

(22) Filed: Oct. 29, 2015

(65) Prior Publication Data

US 2016/0235317 A1   Aug. 18, 2016

Related U.S. Application Data

(60) Provisional application No. 62/117,785, filed on Feb. 18, 2015.

(51) Int. Cl.
*A61N 1/39* (2006.01)
*A61B 5/046* (2006.01)
(Continued)

(52) U.S. Cl.
CPC .............. *A61B 5/046* (2013.01); *A61B 5/04* (2013.01); *A61B 5/04012* (2013.01);
(Continued)

(58) Field of Classification Search
CPC .......... A61B 5/046; A61B 5/042; A61B 5/04; A61B 5/04017; A61B 5/04014;
(Continued)

(56) References Cited

U.S. PATENT DOCUMENTS

| 4,226,245 A | 10/1980 | Bennett, Jr. |
| 4,374,382 A | 2/1983 | Markowitz |

(Continued)

FOREIGN PATENT DOCUMENTS

| EP | 2572634 | 3/2013 |
| WO | 2009809241 | 3/1998 |

(Continued)

OTHER PUBLICATIONS

Couceiro et al., "Detection of Atrial Fibrillation Using Model-Based ECG Analysis", 19th International Conference on Pattern Recognition, Dec. 2008, 5 pages.

(Continued)

*Primary Examiner* — Rex R Holmes

(57) ABSTRACT

An implantable medical device and method for determining an atrial arrhythmia event that includes a cardiac sensing device comprising a housing having circuitry positioned therein, a plurality of electrodes electrically coupled to the circuitry to sense a cardiac signal, and a processor configured to generate an initial detection of an atrial arrhythmia event in response to an atrial arrhythmia threshold, determine whether a P-wave occurs during the initial detection, determine an adaptive threshold in response to the P-wave being detected, adjust the atrial arrhythmia threshold in response to the adaptive threshold, and generate a subsequent initial detection of an atrial arrhythmia event using the adjusted atrial arrhythmia threshold.

28 Claims, 10 Drawing Sheets

(51) Int. Cl.
*A61B 5/04* (2006.01)
*A61B 5/0456* (2006.01)
*A61B 5/00* (2006.01)
*A61N 1/365* (2006.01)
*A61N 1/362* (2006.01)
*A61B 5/0452* (2006.01)
*A61B 5/0464* (2006.01)

(52) U.S. Cl.
CPC ...... *A61B 5/04014* (2013.01); *A61B 5/04017* (2013.01); *A61B 5/0452* (2013.01); *A61B 5/0456* (2013.01); *A61B 5/686* (2013.01); *A61N 1/3624* (2013.01); *A61N 1/36507* (2013.01); *A61N 1/36592* (2013.01); *A61N 1/395* (2013.01); *A61N 1/3987* (2013.01); *A61B 5/0464* (2013.01)

(58) Field of Classification Search
CPC ... A61B 5/686; A61B 5/0456; A61B 5/04012; A61B 5/0464; A61N 1/36507; A61N 1/395; A61N 1/3624; A61N 1/36592; A61N 1/3987
See application file for complete search history.

(56) References Cited

U.S. PATENT DOCUMENTS

| | | | |
|---|---|---|---|
| 4,721,114 A | 1/1988 | DuFault et al. | |
| 5,117,824 A | 6/1992 | Keimel et al. | |
| 5,193,535 A | 3/1993 | Bardy et al. | |
| 5,292,338 A | 3/1994 | Ihara | |
| 5,312,445 A | 5/1994 | Nappholz et al. | |
| 5,334,221 A | 8/1994 | Bardy | |
| 5,458,623 A | 10/1995 | Lu et al. | |
| 5,466,245 A | 11/1995 | Spinelli et al. | |
| 5,545,186 A | 8/1996 | Olson et al. | |
| 5,609,157 A | 3/1997 | Panescu | |
| 5,755,739 A | 5/1998 | Sun et al. | |
| 5,782,888 A | 7/1998 | Sun | |
| 5,817,134 A | 10/1998 | Greenhut et al. | |
| 6,067,473 A | 5/2000 | Greeninger et al. | |
| 6,393,316 B1 | 5/2002 | Gillberg et al. | |
| 6,470,210 B1 | 10/2002 | Chen et al. | |
| 6,516,225 B1 | 2/2003 | Florio | |
| 6,745,068 B2 | 6/2004 | Koyrakh et al. | |
| 6,865,414 B1 | 3/2005 | Levine | |
| 6,895,272 B2 | 5/2005 | Seim et al. | |
| 6,904,315 B2 | 6/2005 | Panken et al. | |
| 6,904,319 B2 | 6/2005 | Seim et al. | |
| 6,912,418 B1 | 6/2005 | Florio | |
| 6,922,584 B2 | 7/2005 | Wang et al. | |
| 6,931,273 B2 | 8/2005 | Sippens | |
| 7,031,765 B2 | 4/2006 | Ritscher et al. | |
| 7,062,315 B2 | 6/2006 | Koyrakh et al. | |
| 7,139,604 B1 | 11/2006 | Mouchawar | |
| 7,184,815 B2 | 2/2007 | Kim et al. | |
| 7,187,965 B2 | 3/2007 | Bischoff et al. | |
| 7,242,978 B2 | 7/2007 | Cao et al. | |
| 7,245,965 B1* | 7/2007 | Pei .................. | A61N 1/3622 128/901 |
| 7,308,308 B1 | 12/2007 | Xi et al. | |
| 7,412,282 B2 | 8/2008 | Houben | |
| 7,509,160 B2 | 3/2009 | Bischoff et al. | |
| 7,515,956 B2 | 4/2009 | Thompson | |
| 7,532,928 B2 | 5/2009 | Lang | |
| 7,537,569 B2 | 5/2009 | Sarkar et al. | |
| 7,561,911 B2 | 7/2009 | Cao et al. | |
| 7,570,990 B2 | 8/2009 | Faber | |
| 7,580,748 B2 | 8/2009 | Garner | |
| 7,593,766 B2 | 9/2009 | Faber | |
| 7,596,405 B2 | 9/2009 | Kurzweil et al. | |
| 7,623,911 B2 | 11/2009 | Sarkar et al. | |
| 7,627,368 B2 | 12/2009 | Houben et al. | |
| 7,640,054 B2 | 12/2009 | Koyrakh et al. | |
| 7,657,305 B2 | 2/2010 | Nigam | |
| 7,657,307 B2 | 2/2010 | Van Dam et al. | |
| 7,706,869 B2 | 4/2010 | Cao et al. | |
| 7,729,754 B2 | 6/2010 | Cao et al. | |
| 7,826,893 B2 | 11/2010 | Cao et al. | |
| 7,983,742 B2 | 7/2011 | Starc | |
| 7,996,070 B2 | 8/2011 | van Dam et al. | |
| 8,000,778 B2 | 8/2011 | Seim et al. | |
| 8,064,998 B2 | 11/2011 | Good | |
| 8,195,280 B2 | 6/2012 | Van Dam et al. | |
| 8,233,980 B2 | 7/2012 | Pei | |
| 8,265,753 B2 | 9/2012 | Higham | |
| 8,280,510 B2 | 10/2012 | Dyjach | |
| 8,285,377 B2 | 10/2012 | Rosenberg | |
| 8,412,316 B2 | 4/2013 | Seim et al. | |
| 8,428,697 B2 | 4/2013 | Zhang et al. | |
| 8,428,705 B2 | 4/2013 | Kurzweil et al. | |
| 8,521,268 B2 | 8/2013 | Zhang et al. | |
| 8,548,573 B2 | 10/2013 | Keefe | |
| 8,560,058 B2 | 10/2013 | Babaeizadeh et al. | |
| 8,588,895 B2 | 11/2013 | Sanghera et al. | |
| 8,639,316 B2 | 1/2014 | Sarkar | |
| 8,688,469 B2 | 4/2014 | Ziegler et al. | |
| 8,718,750 B2 | 5/2014 | Lian | |
| 8,923,963 B2 | 12/2014 | Bonner et al. | |
| 8,977,350 B2 | 3/2015 | Sarkar et al. | |
| 2003/0023178 A1 | 1/2003 | Bischoff et al. | |
| 2005/0065564 A1 | 3/2005 | Seim et al. | |
| 2005/0080347 A1 | 4/2005 | Sheth et al. | |
| 2006/0074332 A1 | 4/2006 | Bischoff et al. | |
| 2006/0079797 A1 | 4/2006 | Bischoff et al. | |
| 2006/0079798 A1 | 4/2006 | Bischoff et al. | |
| 2006/0106323 A1 | 5/2006 | Bischoff et al. | |
| 2007/0142866 A1 | 6/2007 | Li et al. | |
| 2007/0232944 A1 | 10/2007 | Ghanem et al. | |
| 2008/0147133 A1 | 6/2008 | Garner | |
| 2008/0154318 A1 | 6/2008 | Albus | |
| 2008/0161703 A1 | 7/2008 | Houben et al. | |
| 2009/0216144 A1 | 8/2009 | Hopenfeld | |
| 2009/0270747 A1 | 10/2009 | van Dam et al. | |
| 2010/0030293 A1 | 2/2010 | Sarkar et al. | |
| 2011/0125206 A1 | 5/2011 | Bornzin et al. | |
| 2011/0301661 A1 | 12/2011 | Seim et al. | |
| 2011/0319949 A1 | 12/2011 | Bardy | |
| 2012/0123232 A1 | 5/2012 | Najarian et al. | |
| 2012/0226179 A1 | 6/2012 | Stadler et al. | |
| 2012/0238891 A1 | 9/2012 | Sarkar et al. | |
| 2012/0238892 A1 | 9/2012 | Sarkar | |
| 2012/0290030 A1 | 11/2012 | Warman et al. | |
| 2013/0172765 A1 | 7/2013 | Stewart | |
| 2014/0155722 A1 | 6/2014 | Greenspan et al. | |
| 2014/0276154 A1 | 9/2014 | Katra et al. | |
| 2014/0350422 A1 | 11/2014 | Stewart | |
| 2014/0378851 A1 | 12/2014 | Frei et al. | |
| 2015/0073295 A1 | 3/2015 | Gordon et al. | |
| 2015/0080752 A1 | 3/2015 | Lian et al. | |
| 2015/0105681 A1 | 4/2015 | Bonan et al. | |
| 2015/0230722 A1 | 8/2015 | Sarkar et al. | |
| 2015/0305642 A1 | 10/2015 | Reinke et al. | |
| 2015/0306375 A1 | 10/2015 | Marshall et al. | |
| 2015/0306410 A1 | 10/2015 | Marshall et al. | |

FOREIGN PATENT DOCUMENTS

| | | |
|---|---|---|
| WO | 2004043538 | 5/2004 |
| WO | 2004108212 | 12/2004 |
| WO | 0180042 A1 | 10/2007 |
| WO | 2012058398 | 5/2012 |

OTHER PUBLICATIONS

Cao et al., Atrial Arrhythmia Episode Detection in a Cardiac Medical Device, U.S. Appl. No. 15/004,202, filed Jan. 22, 2016, 74 pages.
(PCT/US2016/018389) PCT Notification of Transmittal of the International Search Report and the Written Opinion of the International Searching Authority, dated Jun. 13, 2016, 12 pages.

(56) References Cited

OTHER PUBLICATIONS (PCT/US2016/018496) PCT Notification of Transmittal of the International Search Report and the Written Opinion of the International Searching Authority, dated Jun. 13, 2016, 11 pages.
(PCT/US2016/018383) PCT Notification of Transmittal of the International Search Report and the Written Opinion of the International Searching Authority, dated May 23, 2016, 12 pages.
(PCT/US2016/018408) PCT Notification of Transmittal of the International Search Report and the Written Opinion of the International Searching Authority, dated May 24, 2016, 13 pages.
(PCT/US2016/014493) PCT Notification of Transmittal of the International Search Report and the Written Opinion of the International Searching Authority, dated Apr. 15, 2016, 14 pages.
Helmet Pürerfellner et al., "P-wave Evidence as a Method for Improving Algorithm to Detect Atrial Fibrillation in Insertable Cardiac Monitors", Heart Rhythm, vol. 11, No. 9, Sep. 2014, pp. 1575-1583.
(PCT/US2016/017683) PCT Notification of Transmittal of the International Search Report and the Written Opinion of the International Searching Authority, dated Jun. 8, 2016, 6 pages.
(PCT/US2016/017686) PCT Notification of Transmittal of the International Search Report and the Written Opinion of the International Searching Authority, dated May 11, 2016, 12 pages.
Pürerfellner et al., "P-Wave Evidence as a Method for Improving Algorithm to Detect Atrial Fibrillation in Insertable Cardiac Monitors", Heart Rhythm, vol. 11, No. 9, Sep. 2014, 9 pages.
Sarkar et al, "Method and Apparatus for Atrial Arrhythmia Episode Detection", U.S. Appl. No. 14/695,135, filed Apr. 24, 2015, 30 pages.
Sarkar et al, "Method and Apparatus for Atrial Arrhythmia Episode Detection", U.S. Appl. No. 14/695,156, filed Apr. 24, 2015, 42 pages.
Sarkar et al, "Method and Apparatus for Atrial Arrhythmia Episode Detection", U.S. Appl. No. 14/695,171, filed Apr. 24, 2015, 38 pages.
Sarkar et al, "Method and Apparatus for Atrial Arrhythmia Episode Detection", U.S. Appl. No. 14/695,111, filed Apr. 24, 2015, 51 pages.
Cao et al, "Atrial Arrhythmia Episode Detection in a Cardiac Medical Device", U.S. Appl. No. 14/604,363, filed Jan. 23, 2015, 46 pages.
Cao et al, "Atrial Arrhythmia Episode Detection in a Cardiac Medical Device", U.S. Appl. No. 14/604,411, filed Jan. 23, 2015, 48 pages.
Cao et al, "Atrial Arrhythmia Episode Detection in a Cardiac Medical Device", U.S. Appl. No. 14/604,468, filed Jan. 23, 2015, 46 pages.
Zhang et al, "Method and Apparatus for Beat Acquisition During Template Generation in a Medical Device Having Dual Sensing Vectors", U.S. Appl. No. 14/604,111, filed Jan. 23, 2015, 77 pages.
Zhang et al, "Method and Apparatus for Beat Acquisition During Template Generation in a Medical Device Having Dual Sensing Vectors", U.S. Appl. No. 14/604,260, filed Jan. 23, 2015, 75 pages.
Zhang et al, "Method and Apparatus for Beat Acquisition During Template Generation in a Medical Device Having Dual Sensing Vectors", U.S. Appl. No. 15/002,521, filed Jan. 21, 2016, 80 pages.
Sarkar et al, "Method and Apparatus for Adjusting a Threshold During Atrial Arrhythmia Episode Detection in an Implantable Medical Device", U.S. Appl. No. 14/926,419, filed Oct. 29, 2015, 51 pages.
SARKAR et al, "Method and Apparatus for Identifying Sick Sinus Syndrome", U.S. Appl. No. 14/926,455, filed Oct. 29, 2015, 39 pages.
Cao et al, "Atrial Arrthytmia Detection During Intermittent Instances of Ventricular Pacing in a Cardiac Medical Device", U.S. Appl. No. 14/520,798, filed Oct. 22, 2014, 35 pages.
Cao et al, "Atrial Arrhythmia Detection During Ventricular Pacing in a Cardiac Medical Device", U.S. Appl. No. 14/520,847, filed Oct. 22, 2014, 49 pages.
Cao et al, "Atrial Arrhythmia Episode Detection in a Cardiac Medical Device", U.S. Appl. No. 14/520,938, filed Oct. 22, 2014, 47 pages.

\* cited by examiner

METHOD AND APPARATUS FOR ADJUSTING A THRESHOLD DURING ATRIAL ARRHYTHMIA EPISODE DETECTION IN AN IMPLANTABLE MEDICAL DEVICE

CROSS-REFERENCE TO RELATED APPLICATIONS

This application claims priority and other benefits of U.S. Provisional Application No. 62/117,785, filed on Feb. 18, 2015, entitled "Method and Apparatus for Atrial Arrhythmia Detection", incorporated herein by reference in its entirety.

TECHNICAL FIELD

The disclosure relates generally to implantable medical devices and, in particular, to a method for and apparatus for adjusting a detection threshold for detecting atrial arrhythmia episodes in an implantable medical device.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

In the past, atrial arrhythmias have been largely undertreated due to the perception that these arrhythmias are relatively benign. As more serious consequences of persistent atrial arrhythmias have come to be understood, such as an associated risk of relatively more serious ventricular arrhythmias and stroke, there is a growing interest in monitoring and treating atrial arrhythmias.

Methods for discriminating arrhythmias that are atrial in origin from arrhythmias originating in the ventricles have been developed for use in dual chamber implantable devices wherein both an atrial EGM signal and a ventricular EGM signal are available. Discrimination of arrhythmias can rely on event intervals (PP intervals and RR intervals), event patterns, and EGM morphology. Such methods have been shown to reliably discriminate ventricular arrhythmias from supra-ventricular arrhythmias. In addition, such methods have been developed for use in single chamber implantable devices, subcutaneous implantable devices, and external monitoring devices, where an adequate atrial EGM signal having acceptable signal-to-noise ratio is not always available for use in detecting and discriminating atrial arrhythmias.

Occasionally, false detection of atrial fibrillation may occur in a cardiac medical device during runs of ectopic rhythm with irregular coupling intervals or underlying sinus variability/sick sinus. In addition, false detection of atrial tachycardia may occur in a cardiac medical device during ectopy and regular normal sinus rhythm. Therefore, what is needed is a method and apparatus for improving detection of atrial tachyarrhythmia to reduce false detection in a cardiac medical device.

DETAILED DESCRIPTION

In the following description, references are made to illustrative embodiments for carrying out the methods described herein. It is understood that other embodiments may be utilized without departing from the scope of the disclosure.

The methods presented herein may be embodied in software, hardware or firmware in implantable or external medical devices. Such devices include implantable monitoring devices having cardiac EGM/ECG monitoring capabilities and associated EGM/ECG sense electrodes, which may be intracardiac, epicardial, or subcutaneous electrodes.

The methods described herein can also be incorporated in implantable medical devices having therapy delivery capabilities, such as single chamber or bi-ventricular pacing systems or ICDs that sense the R-waves in the ventricles and deliver an electrical stimulation therapy to the ventricles. The atrial arrhythmia detection methods presently disclosed may also be incorporated in external monitors having ECG electrodes coupled to the patient's skin to detect R-waves, e.g. Holter monitors, or within computerized systems that analyze pre-recorded ECG or EGM data. Embodiments may further be implemented in a patient monitoring system, such as a centralized computer system which processes data sent to it by implantable or wearable monitoring devices, including subcutaneous devices having loop recorders.

Figure 1:
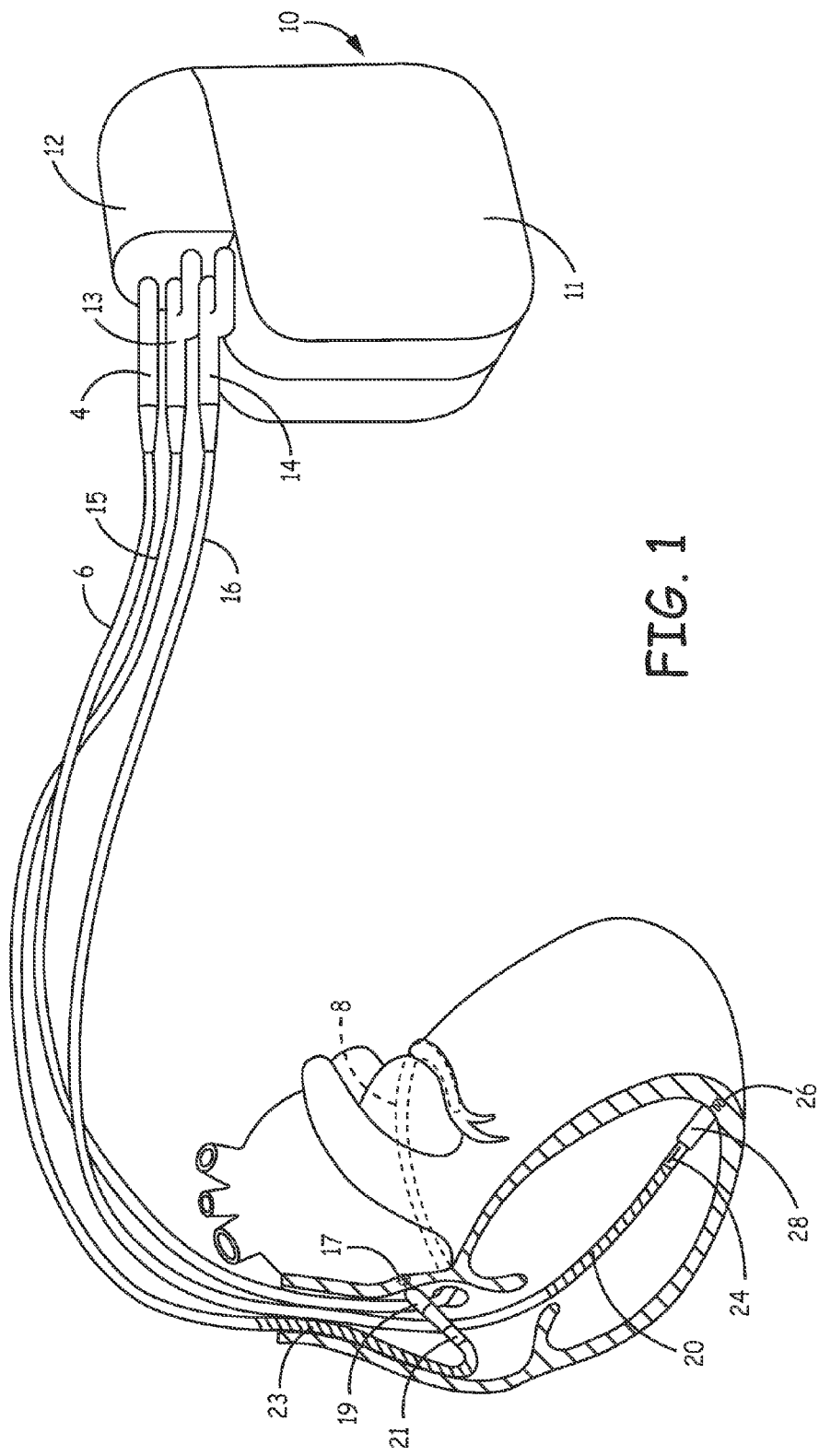
FIG. 1 is a schematic diagram of an exemplary medical device for detecting an arrhythmia according to an embodiment of the present disclosure.

FIG. 1 is a schematic diagram of an exemplary medical device for detecting an arrhythmia according to an embodiment of the present disclosure. As illustrated in FIG. 1, an implantable medical device 10 according to an embodiment of the present disclosure may be in the form of an implantable cardioverter defibrillator (ICD) 10 a connector block 12 that receives the proximal ends of a right ventricular lead 16, a right atrial lead 15 and a coronary sinus lead 6, used for positioning electrodes for sensing and stimulation in three or four heart chambers. Right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10. It is understood that although the device illustrated in FIG. 1 is a dual chamber device, other devices such as single chamber devices may be utilized to perform the technique of the present disclosure described herein.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as true bipolar pairs, commonly referred to as a "tip-to-ring" configuration. Further, electrode 17 and coil electrode 20 or electrode 24 and coil electrode 23 may be used as integrated bipolar pairs, commonly referred to as a "tip-to-coil" configuration. In accordance with the invention, ICD 10 may, for example, adjust the electrode configuration from a tip-to-ring configuration, e.g., true bipolar sensing, to a tip-to-coil configuration, e.g., integrated bipolar sensing, upon detection of oversensing in order to reduce the likelihood of future oversensing. In other words, the electrode polarities can be reselected in response to detection of oversensing in an effort to reduce susceptibility of oversensing. In some cases, electrodes 17, 21, 24, and 26 may be used individually in a unipolar configuration with the device housing 11 serving as the indifferent electrode, commonly referred to as the "can" or "case" electrode.

The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may adapted for use with any single chamber, dual chamber, or multi-chamber ICD or pacemaker system, subcutaneous implantable device, or other internal or external cardiac monitoring device.

ICD 10 may alternatively be configured as a subcutaneous device having sensing or pacing electrodes incorporated on the housing 11 of the device in which case transvenous leads are not required. A subcutaneous device may be coupled to a lead tunneled subcutaneously or submuscularly for delivering transthoracic pacing pulses and/or sensing ECG signals. An exemplary subcutaneous device is described in commonly assigned U.S. patent application Ser. Nos. 14/604,111 and 14/604,260, both incorporated herein by reference in their entireties. The techniques described herein can also be implemented in an external device, e.g. including patch electrodes and optionally another physiological sensor if desired, that can sense variable parameters as described herein.

Figure 2:
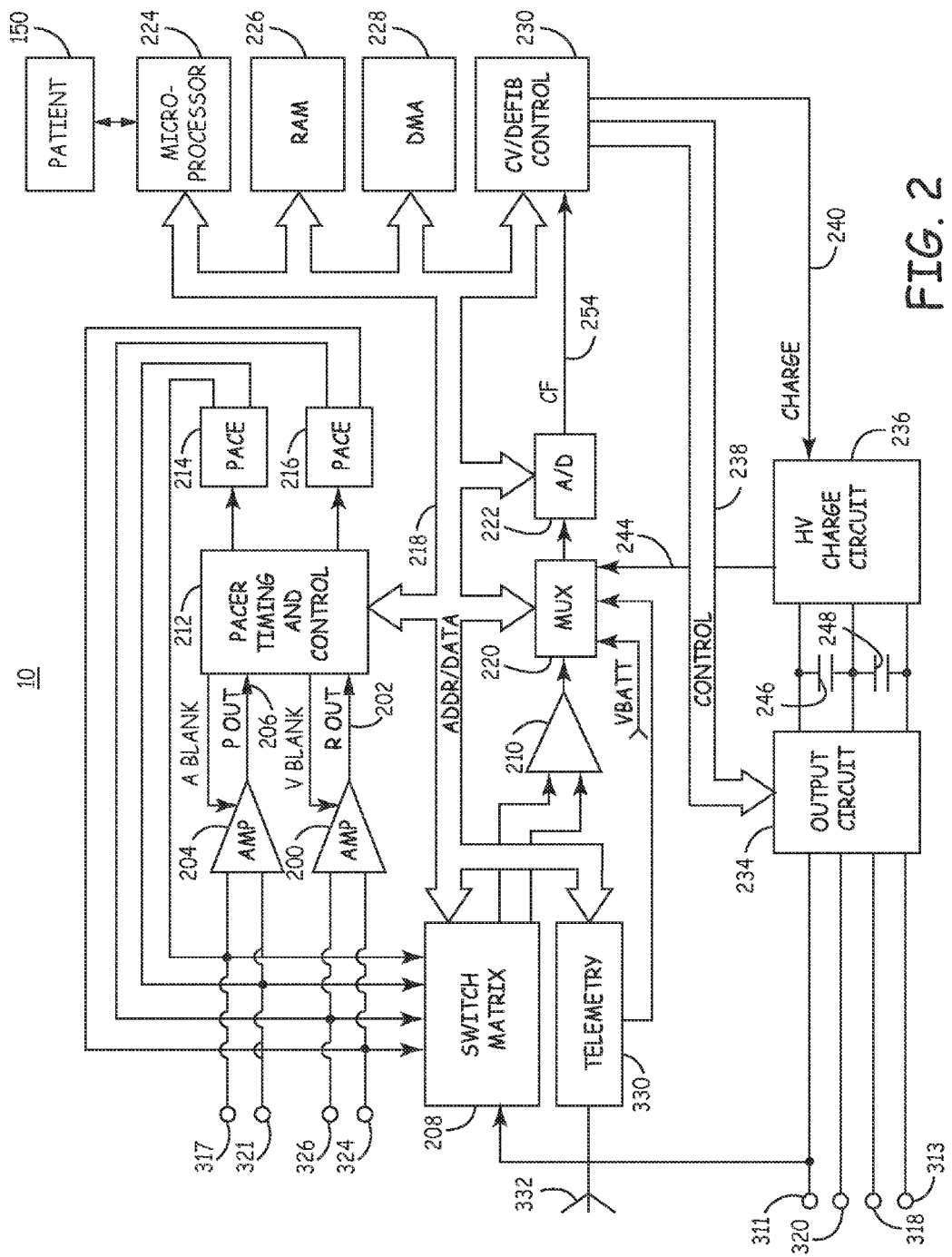
FIG. 2 is a functional schematic diagram of the medical device of FIG. 1.

FIG. 2 is a functional schematic diagram of the medical device of FIG. 1. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, ICD 10 is provided with a number of connection terminals for achieving electrical connection to the leads 6, 15, and 16 and their respective electrodes. A connection terminal 311 provides electrical connection to the housing 11 for use as the indifferent electrode during unipolar stimulation or sensing. The connection terminals 320, 313, and 318 provide electrical connection to coil electrodes 20, 8 and 23 respectively. Each of these connection terminals 311, 320, 313, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals. The atrial sense amplifier 204 and the ventricular sense amplifier 200 preferably take the form of automatic gain controlled amplifiers with adjustable sensitivity. In accordance with the invention, ICD 10 and, more specifically, microprocessor 224 automatically adjusts the sensitivity of atrial sense amplifier 204, ventricular sense amplifier 200 or both in response to detection of oversensing in order to reduce the likelihood of oversensing. Ventricular sense amplifier 200 and atrial sense amplifier 204 operate in accordance with originally programmed sensing parameters for a plurality of cardiac cycles, and upon detecting oversensing, automatically provides the corrective action to avoid future oversensing. In this manner, the adjustments provided by ICD 10 to amplifiers 200 and 204 to avoid future oversensing are dynamic in nature. Particularly, microprocessor 224 increases a sensitivity value of the amplifiers, thus reducing the sensitivity, when oversensing is detected. Atrial sense amplifier 204 and ventricular sense amplifier 200 receive timing information from pacer timing and control circuitry 212.

Specifically, atrial sense amplifier 204 and ventricular sense amplifier 200 receive blanking period input, e.g., ABLANK and VBLANK, respectively, which indicates the amount of time the electrodes are "turned off" in order to prevent saturation due to an applied pacing pulse or defibrillation shock. As will be described, the blanking periods of atrial sense amplifier 204 and ventricular sense amplifier 200 and, in turn, the blanking periods of sensing electrodes associated with the respective amplifiers may be automatically adjusted by ICD 10 to reduce the likelihood of oversensing. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Specifically, microprocessor 224 may modify the electrode configurations based on detection of oversensing due to cardiac or non-cardiac origins. Upon detection of R-wave oversensing, for example, microprocessor 224 may modify the electrode configuration of the right ventricle from true bipolar sensing, e.g., tip-to-ring, to integrated bipolar sensing, e.g., tip-to-coil.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228 via data/address bus 218. Microprocessor 224 may employ digital signal analysis techniques to characterize the digitized signals stored in random access memory 226 to recognize and classify the patient's heart rhythm employing any of the numerous signal processing methodologies known in the art. An exemplary tachyarrhythmia recognition system is described in U.S. Pat. No. 5,545,186 issued to Olson et al, incorporated herein by reference in its entirety.

Upon detection of an arrhythmia, an episode of EGM data, along with sensed intervals and corresponding annotations of sensed events, are preferably stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 26 and 24. A far-field sensing electrode pair includes electrodes spaced further apart such as any of: the defibrillation coil electrodes 8, 20 or 23 with housing 11; a tip electrode 17 or 26 with housing 11; a tip electrode 17 or 26 with a defibrillation coil electrode 20 or 23; or atrial tip electrode 17 with ventricular ring electrode 24. The use of near-field and far-field EGM sensing of arrhythmia episodes is described in U.S. Pat. No. 5,193,535, issued to Bardy, incorporated herein by reference in its entirety. Annotation of sensed events, which may be displayed and stored with EGM data, is described in U.S. Pat. No. 4,374,382 issued to Markowitz, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia. In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
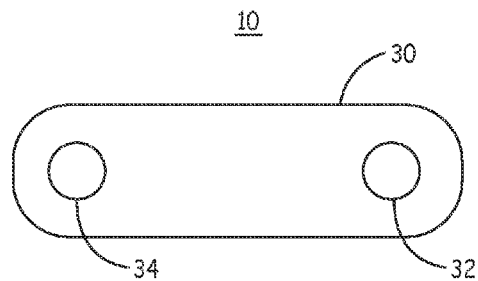
FIG. 3 is a conceptual diagram of an example of an implantable medical device for detecting an arrhythmia event, according to another embodiment of the present disclosure.

FIG. 3 is a conceptual diagram of an example of an implantable medical device for detecting an arrhythmia event, according to another embodiment of the present disclosure. As illustrated in FIG. 3, according to another embodiment, the implantable medical device 10 may be embodied as a monitoring device having a proximal electrode 32 and a distal electrode 34 located along a housing 30 of the monitoring device 10, as described for example, in U.S. Patent Publication No. 2015/0073295, incorporated herein by reference in it's entirety. The housing 30 encloses electronic circuitry inside the implantable medical device 10 and protects the implantable medical device circuitry contained therein (shown in FIG. 4) from body fluids. Electrical feedthroughs provide electrical connection of electrodes 32 and 34 across the housing 30 to internal circuitry when electrodes 32 and 34 are positioned along the exterior surface of housing 30.

The implantable medical device 10 may be embodied as an implantable cardiac monitor wherein electrodes 32 and 34 are used to sense cardiac signals for determining an atrial arrhythmia event, described below, e.g. ECG signals, intra-thoracically or extra-thoracically, which may be sub-muscularly or subcutaneously. ECG signals may be stored in a memory (shown in FIG. 4) of the implantable medical device 10, and ECG data may be transmitted by the implantable medical device 10 to another medical device, which may be another implantable device or an external device. In alternative applications, electrodes 32 and 34 may be used for sensing any biopotential signal of interest, which may be, for example, an EGM, EEG, EMG, or a nerve signal, from any implanted location.

The implantable medical device 10 may be further configured to use electrodes 32 and 34 for measuring bioimpedance across electrodes 32 and 34 when implanted in a patient's body. The bioimpedance is the impedance of the body tissue and/or fluid present in a measurement volume adjacent to electrodes 32 and 34. The bioimpedance may be used for monitoring volume, pressure, fluid status, or other tissue or fluid changes that cause a change in impedance between electrodes 32 and 34.

Electrodes 32 and 34 may be formed of a biocompatible conductive material, e.g. titanium, platinum, iridium, or alloys thereof. The configuration illustrated in FIG. 3 is just one example electrode configuration. In other instances, sensing electrodes 32 and 34 may be located at other positions along the housing 30 than the positions shown in FIG. 3. For example, the electrodes 32 and 34 are shown both positioned along a top side of the implantable medical device 10, but in other examples electrodes 32 and 34 may be located on the bottom side or lateral side of the implantable medical device 10, on opposing sides of the implantable medical device 10, or on one or both ends of the implantable medical device 10. Additionally, all or a portion of the housing 30 may function as one of the electrodes and be insulated from any other electrodes positioned along the housing 30. An exemplary description of such a configuration is disclosed in commonly assigned and co-pending U.S. patent application Ser. No. 14/060,649, titled "Supply Noise Rejection In Implantable Medical Devices" (Reinke et al.), incorporated herein by reference in its entirety. In still other embodiments, an implantable medical device may include one or more electrodes carried by an electrical lead or tether extending away from the implantable medical device and coupled to the implantable medical device internal circuitry via electrical feedthroughs and conductors. In further instances, implantable medical device 10 may include more than two electrodes for various monitoring or therapy delivery purposes, but a single pair of electrodes is used for both delivering a drive signal for measuring a tissue bioimpedance and for receiving a biopotential signal. The bioimpedance signal is also received from the same pair of electrodes. In other examples, the bioimpedance signal may be sensed from a different pair of recording electrodes than the single pair of electrodes used to apply the drive signal and receive the bioimpedance signal.

Although illustrated and described throughout this disclosure as being a cardiac monitor, the implantable medical device 10 may be any of number of other implantable devices, including implantable hemodynamic monitors, blood chemistry monitors, pressure monitors, nerve monitors, muscle monitors, brain monitors, or the like. In any of these cases, the implantable medical device 10 may include additional sensors besides electrodes 32 and 34 to monitor desired physiological signals.

Figure 4:
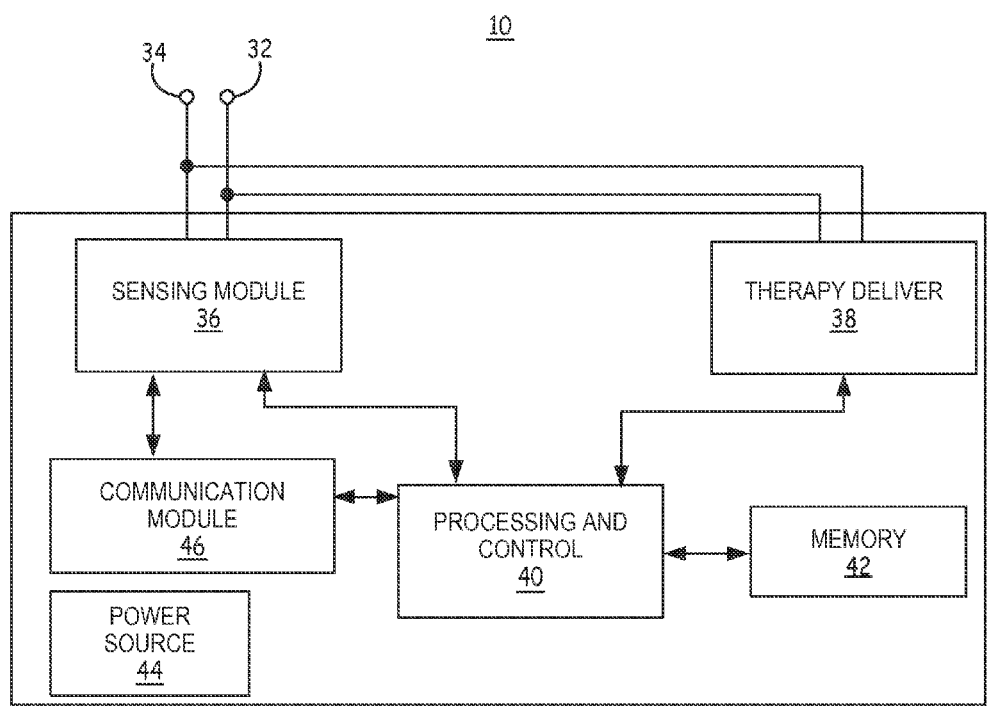
FIG. 4 is a functional schematic diagram of the medical device of FIG. 3, according to an embodiment of the present disclosure.

FIG. 4 is a functional block diagram of the implantable medical device 10 shown in FIG. 3. The implantable medical device 10 includes a cardiac signal sensing module 36 coupled to electrodes 32 and 34 for sensing cardiac signals and monitoring atrial arrhythmia events, such as atrial fibrillation or atrial tachycardia within a patient, as described below.

The implantable medical device 10 may be embodied as a monitoring-only device without therapy delivery capabilities. In other examples, the implantable medical device 10 may include a therapy delivery module 38, which may be configured to generate electrical pulses for delivering therapeutic electrical stimulation, such as cardiac pacing, nerve stimulation, deep brain stimulation, or other neurostimulation. In such examples, therapy delivery module 38 is coupled to electrodes 32 and 34 for delivering electrical pulses to achieve a therapeutic benefit to the patient in addition to monitoring biopotential and bioimpedance signals of the patient. Sensing cardiac signals during therapeutic stimulation pulse delivery may be temporarily blanked or interrupted to prevent saturation of sensing amplifiers during stimulation pulse delivery. Other examples of therapy delivery capabilities that may be included in therapy delivery module 38 include fluid delivery pumps for delivering a pharmacological agent, biological fluid or other therapeutic fluid.

The sensing module 30 may include an analog amplifier and/or filter for receiving an analog voltage signal from electrodes 32 and 34. The analog voltage signals received from electrodes 32 and 34 are passed to analog-to-digital (A/D) converters included in the sensing module 30 or in processing and control module 40. The A/D converters provide a sampled, digital signal of the cardiac signal received by the sensing module 30 to processing and control module 40 for further analysis according to a particular clinical application and/or storage in memory 42.

Processing and control module 40 and associated memory 42 control implantable medical device functions and process signals received from electrodes 32 and 34 according to programmed signal analysis routines or algorithms. The implantable medical device 10 may include other optional sensors (not shown) for monitoring physiological signals, such as an activity sensor, pressure sensor, oxygen sensor, accelerometer, or other sensor used to monitor a patient.

Processing and control module 40 may control monitoring time intervals and sampling rates according to a particular clinical application. Processing and control module 40 may include state machines or other sequential logic circuitry to control device functions and need not be implemented exclusively as a microprocessor. Processor and control module 40 and sensing module 20 may operate to acquire signal data and store processed or raw signal data in memory 42.

Communication module 46 includes an antenna and wireless transmitter to transmit electrical signal data, e.g. ECG signal data, stored in memory 42 or received from processing and control module 40 in real time. Communication module 46 may be configured to transmit and receive communication signals via inductive coupling, electromagnetic coupling, tissue conductance, Near Field Communication (NFC), Radio Frequency Identification (RFID), BLUETOOTH®, WiFi, or other proprietary or non-proprietary wireless telemetry communication schemes. Communication module enables the monitoring device 10 to communicate with a programmer (not shown) located external to the device 10 and includes a user interface that presents information to and receives input from a user. It should be noted that the user may also interact with programmer remotely via a networked computing device.

A user, such as a physician, technician, surgeon, electrophysiologist, other clinician, or patient, interacts with programmer to communicate with monitoring device 10. For example, the user may interact with programmer to retrieve physiological or diagnostic information from monitoring device 10. A user may also interact with programmer to program monitoring device 10, e.g., select values for operational parameters of the monitoring device 10. For example, the user may use programmer to retrieve information from monitoring device 10 regarding the rhythm of a patient heart, trends therein over time, or arrhythmic episodes. Monitoring device 10 and the programmer may communicate via wireless communication using any techniques known in the art.

A power source 44 provides power to each of the modules 36, 38, 40, 46, and memory 42 as needed. Power source 44 may include one or more energy storage devices, such as one or more rechargeable or non-rechargeable batteries.

Modules 36, 38, 40, 46, and memory 42 represent functionality included in the implantable medical device 10. Modules of the present disclosure may include any discrete and/or integrated electronic circuit components that implement analog and/or digital circuits capable of producing the functions attributed to the modules herein. For example, the modules may include analog circuits, e.g., pre-amplification circuits, filtering circuits, and/or other analog signal conditioning circuits. The modules may also include digital circuits, e.g., digital filters, combinational or sequential logic circuits, state machines, integrated circuits, a processor (shared, dedicated, or group) that executes one or more software or firmware programs, memory devices, or any other suitable components or combination thereof that provide the described functionality.

Memory 42 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), Flash memory, or any other memory device. Memory 42 may include non-transitory computer readable storage media storing instructions that, when executed by one or more processing circuits, cause the modules to perform various functions attributed to the implantable medical device 10. The storage media may include any computer-readable storage media with the sole exception being a transitory, propagating signal.

Depiction of different features as modules is intended to highlight different functional aspects and does not necessarily imply that such modules must be realized by separate hardware or software components. Rather, functionality associated with one or more modules may be performed by separate hardware, firmware and/or software components, or integrated within common hardware, firmware and/or software components.

Figure 5:
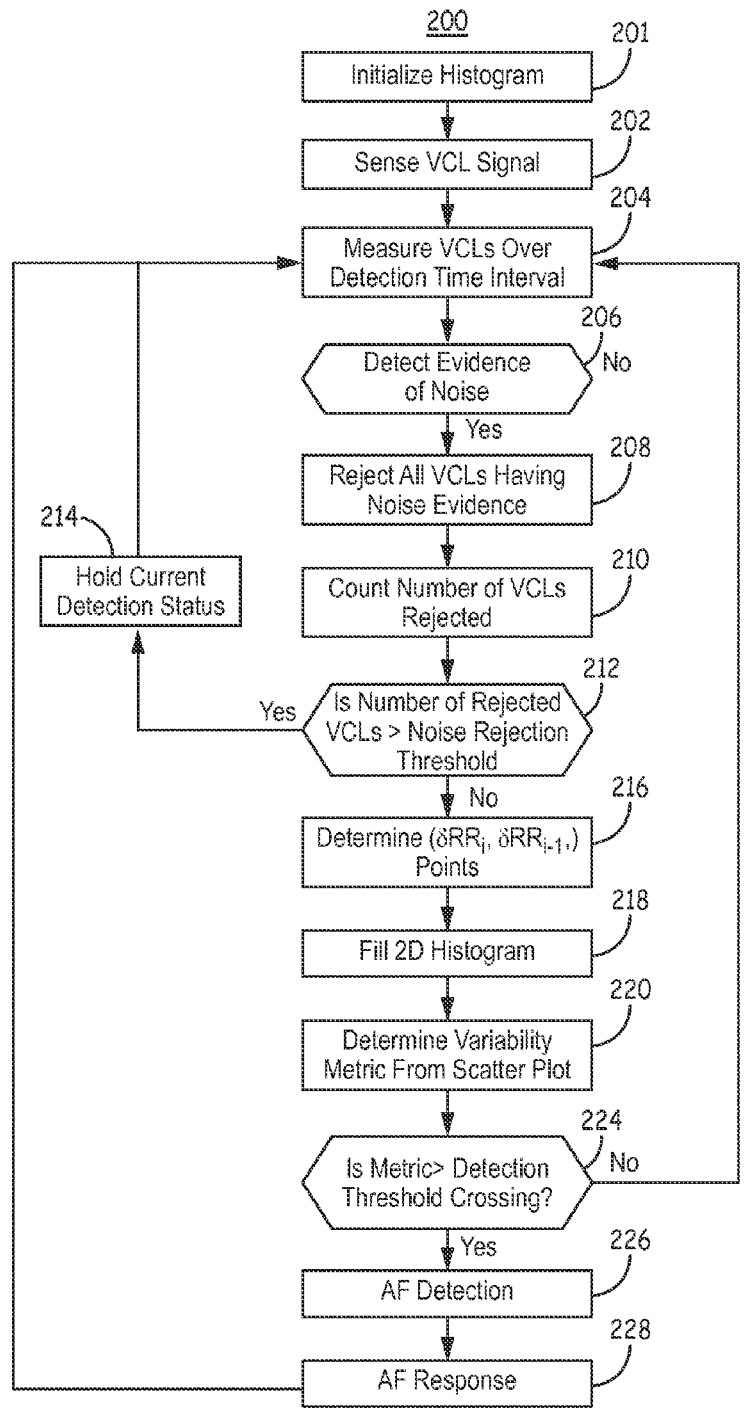
FIG. 5 is an exemplary flowchart of a method for detecting an atrial arrhythmia according to an embodiment of the disclosure.

FIG. 5 is an exemplary flowchart of a method for detecting an atrial arrhythmia according to an embodiment of the disclosure. Flow chart 200 illustrated in FIG. 5 and other flow charts presented herein are intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern implantable medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Flow chart 200 is directed to atrial fibrillation (AF) detection, however it is recognized that aspects of the method may be applied to detection of other atrial arrhythmias, such as atrial flutter or other forms of atrial tachycardia. According to an embodiment of the present disclosure, the device includes a method and apparatus for detecting an atrial arrhythmia, such as atrial fibrillation or atrial flutter, for example. As illustrated in FIG. 5, according to one embodiment, the determination of an atrial arrhythmia may be based on the irregularity of ventricular cycles having RR intervals that exhibit discriminatory signatures when plotted in a Lorenz scatter plot, such as is generally disclosed by Ritscher et al. in U.S. Pat. No. 7,031,765, or in U.S. Pat. No. 8,639,316 to Sarkar, both incorporated herein by reference in their entireties. Other atrial arrhythmia determination methods are generally disclosed by Sarkar, et al. in U.S. Pat. No. 7,623,911 and in U.S. Pat. No. 7,537,569, and by Houben in U.S. Pat. No. 7,627,368, all of which patents are also incorporated herein by reference in their entireties.

In particular, at block 201, a histogram is initialized by defining the number of histogram bins for each coordinate axis and corresponding bin ranges. A counter for each histogram bin is set to zero. At block 202, a physiological signal containing VCL information is obtained. The signal may be an EGM or ECG signal but is not limited to being a cardiac electrical signal.

At block 204 the VCL intervals, e.g. RRIs, are collected over a predetermined rhythm detection time interval, for example for 2 minutes. Data collected over the established detection time interval is used to classify the rhythm at the end of the detection time interval. At block 206, a noise detection analysis is performed to detect evidence that a sensed R-wave signal or measured RRI contains noise artifact. Numerous noise detection methods may be used. Evidence of noise may detected based on frequency content, amplitude content, or VCL measurements themselves.

If no evidence of noise is detected in the predetermined time interval, the ($\delta RR_i$, $\delta RR_{i-1}$) data points are computed from the measured VCLs at block 216. If evidence of noise is detected, the VCLs that are associated with noise evidence are rejected at block 208. Any ($\delta RR_i$, $\delta RR_{i-1}$) data points that involve an RRI that is rejected will be skipped. Depending on the noise detection method being used, evidence of noise may be detected during the RRI between sensed R-waves or a sensed R-wave itself may be detected as noise. If a sensed R-wave is determined to be noise, both the preceding and subsequent RRIs defined by the sensed R-wave may be rejected as noise intervals.

The number of rejected VCLs is counted at block 210. The total number of VCLs (e.g. RRIs) rejected during the detection time interval due to noise is compared to a noise rejection threshold at block 212. If the noise rejection threshold is exceeded, the current rhythm detection status is held at block 214. The current time interval is considered to be too noisy for use in rhythm detection and no change in the status of the currently detected rhythm will be made based on the VCLs measured during the current time interval. For example, if the implantable medical device detected AF at the end of the last detection time interval based on the analysis of histogram counts, the AF detection will be maintained at the end of the current time interval. If the implantable medical device is not detecting AF at the end of the previous detection time interval, the implantable medical device remains in a state of no AF detection at the end of the current time interval. The current detection time interval is rejected as a whole for rhythm determination and classification. The process returns to block 204 to measure VCLs over the next detection time interval.

If the number of rejected cycle lengths has not reached a noise rejection threshold (block 212), the current detection time interval data is still used to populate a histogram defining a Lorenz plot area. At block 216, the ($\delta RR_i$, $\delta RR_{i-1}$) data points are determined using only RRIs that are not associated with noise evidence detection. Rejected RRIs are not used to compute RRI differences or ($\delta RR_i$, $\delta RR_{i-1}$) data points determined using rejected RRIs are skipped when populating the histogram. In this way, RRIs associated with noise aren't included in the analysis of VCLs in the Lorenz plot histogram. The remainder of the VCLs that are not rejected during the detection time interval are used for determining ($\delta RR_i$, $\delta RR_{i-1}$) data points. All ($\delta RR_i$, $\delta RR_{i-1}$) data points points not involving a rejected RRI may be used to populate the histogram. If a non-rejected VCL is sandwiched between two rejected VCLs, the VCL is not used because no adjacent non-rejected VCL is available for computing consecutive RRI differences for determining a valid ($\delta RR_i$, $\delta RR_{i-1}$) data point.

As described previously, a 2D scatter plot is generated wherein each point is defined by an x-coordinate corresponding to the difference between an RRI and the previous RRI and the y-coordinate corresponding to the difference between the previous RRI and the next previous RRI. The histogram is filled by incrementing a counter for the histogram bin which corresponds to the coordinate values of each ($\delta RR_i$, $\delta RR_{i-1}$) data point. The methods described herein are generally implemented using a 2D histogram, however aspects of the invention may alternatively be implemented in methods using 1D or higher dimensional scatter plots of VCL data.

At block 220 an RRI variability metric (or more generally a VCL variability metric) is determined from the scatter plot. Generally, the more histogram bins that are occupied, i.e. the more sparse the distribution of ($\delta RR_i$, $\delta RR_{i-1}$) points, the more irregular the VCL during the data acquisition time period. As such, a metric of the RRI variability can be used for detecting atrial fibrillation, which is associated with highly irregular VCL. In one embodiment, an RRI variability metric for detecting AF, referred to as an AF score is computed as generally described in the above-incorporated '911 patent. Briefly, the AF score may be defined by the equation:

$$\text{AF Evidence} = \text{Irregularity Evidence} - \text{Origin Count} - \text{PAC Evidence}$$

wherein Irregularity Evidence is the number of occupied histogram bins outside a Zero Segment defined around the origin of the Lorenz plot area. During normal sinus rhythm or highly organized atrial tachycardia, nearly all points will fall into the Zero Segment because of relatively small, consistent differences between consecutive RRIs. A high number of occupied histogram bins outside the Zero segment is therefore positive evidence for AF.

The Origin Count is the number of points in a "Zero Segment" defined around the Lorenz plot origin. A high Origin Count indicates regular RRIs, a negative indicator of AF, and is therefore subtracted from the Irregularity Evidence term. In addition, a regular PAC evidence score may be computed as generally described in the above-incorporated '911 patent. The regular PAC evidence score is computed based on a cluster signature pattern of data points that is particularly associated with PACs that occur at regular coupling intervals and present regular patterns of RRIs, e.g. associated with bigeminy (short-short-long RRIs) or trigeminy (short-short-short-long RRIs).

In other embodiments, an AF score or other RRI variability score for classifying an atrial rhythm may be computed as described in any of the above-incorporated '765, '911, '569 and '368 patents.

The AF score will be compared to an interval variation threshold for detecting AF, or AF detection threshold, at Block 224. If the metric crosses, i.e., the AF score is greater than the interval variation threshold, AF detection is made at block 226. A response to AF detection is made at block 228, which may include withholding a ventricular therapy, storing data, or triggering other signal acquisition or analysis, as described below. The AF response may be to generate a patient alarm or deliver or adjust a therapy. The RRI measurements continue to be performed after an AF detection to fill the histogram during the next detection time interval by returning to block 204.

After each detection time interval, the RRI variability metric is determined and the histogram bins are re-initialized to zero for the next detection time interval. The new RRI variability metric determined at the end of each data acquisition interval may be used to determine if the AF episode is sustained or terminated.

Figure 6:
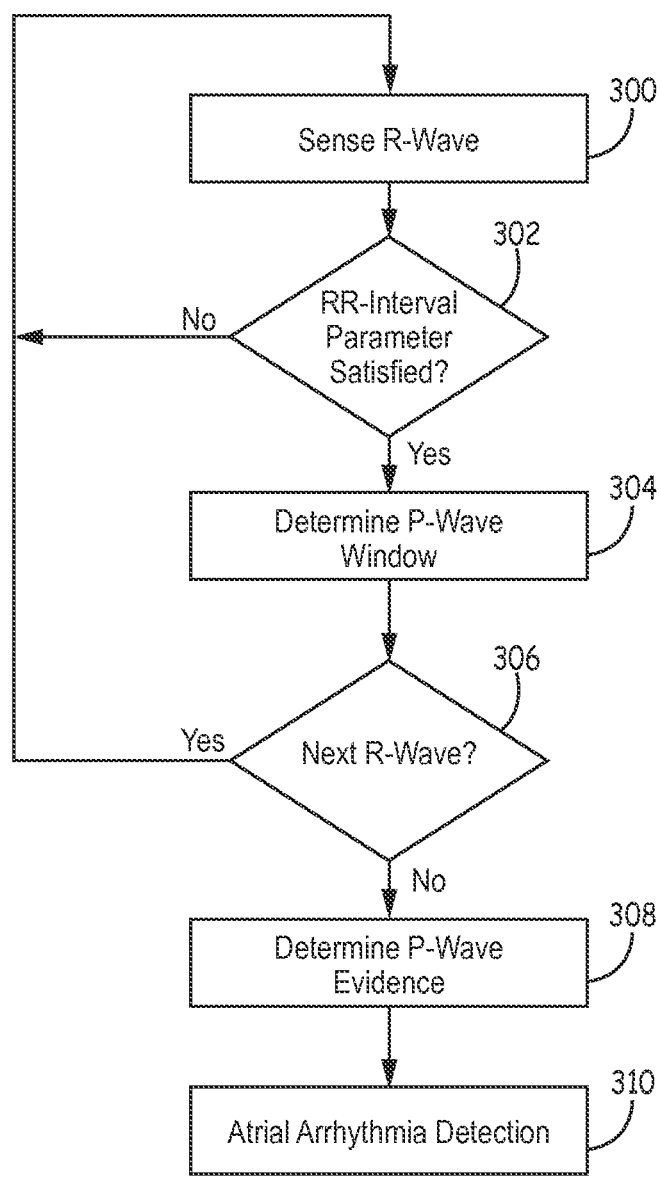
FIG. 6 is a flowchart of a method of augmenting detection of an atrial arrhythmia according to an embodiment of the present invention.

FIG. 6 is a flowchart of a method of augmenting detection of an atrial arrhythmia according to an embodiment of the present invention. As illustrated in FIG. 6, according to an embodiment of the present application, in order to determine whether a sensed cardiac signal is an atrial tachycardia event, once an AF event is determined to occur, the device determines whether the cardiac signal contains a P-wave portion, the results of which are utilized to augment the atrial tachycardia determination process described above. As illustrated in FIG. 6, according to one embodiment, during determination of signal characteristics for augmenting atrial tachycardia detection, the device senses the cardiac signal and identifies R-waves in response to the sensed cardiac signal using any known cardiac signal sensing and detection scheme, such as that disclosed in U.S. Pat. No. 5,117,824, by Keimel, et al., for example, described above and incorporated herein by reference in its entirety. Upon detection of an R-wave associated with the sensed cardiac signal, Block 300, the device determines whether the R-wave satisfies one or more RR-interval parameters, Block 302, described below. If the RR-interval parameter or parameters are not satisfied, No in Block 302, the device waits for the next sensed R-wave, Block 300 and the process Block 300-302 is repeated using the next R-wave. If the RR-interval parameter or parameters are satisfied, Yes in Block 302, the device determines a P-wave window associated with the R-wave, Block 304, as described below.

Upon determination of the P-wave window, the device determines whether a predetermined number of R-waves have been identified, Block 306. The predetermined number of R-waves required to satisfy the determination in Block 306 may be set as one or more R-waves, and according to one embodiment is set as four R-waves for example. If the predetermined number of R-waves have not been identified and therefore a next R-wave is needed, Yes in Block 306, the device waits for the next sensed R-wave, Block 300 and the process Block 300-306 is repeated using the next R-wave. If the predetermined number of R-waves have been identified and therefore a next R-wave is not needed, No in Block 306, the device determines P-wave evidence, Block 308, described below, and utilizes the determined P-wave evidence to augment atrial arrhythmia detection, Block 310, as described, for example, in commonly assigned U.S. patent application Ser. No. 14/695,111 to Sarkar et al., incorporated herein by reference in it's entirety.

Figure 7:
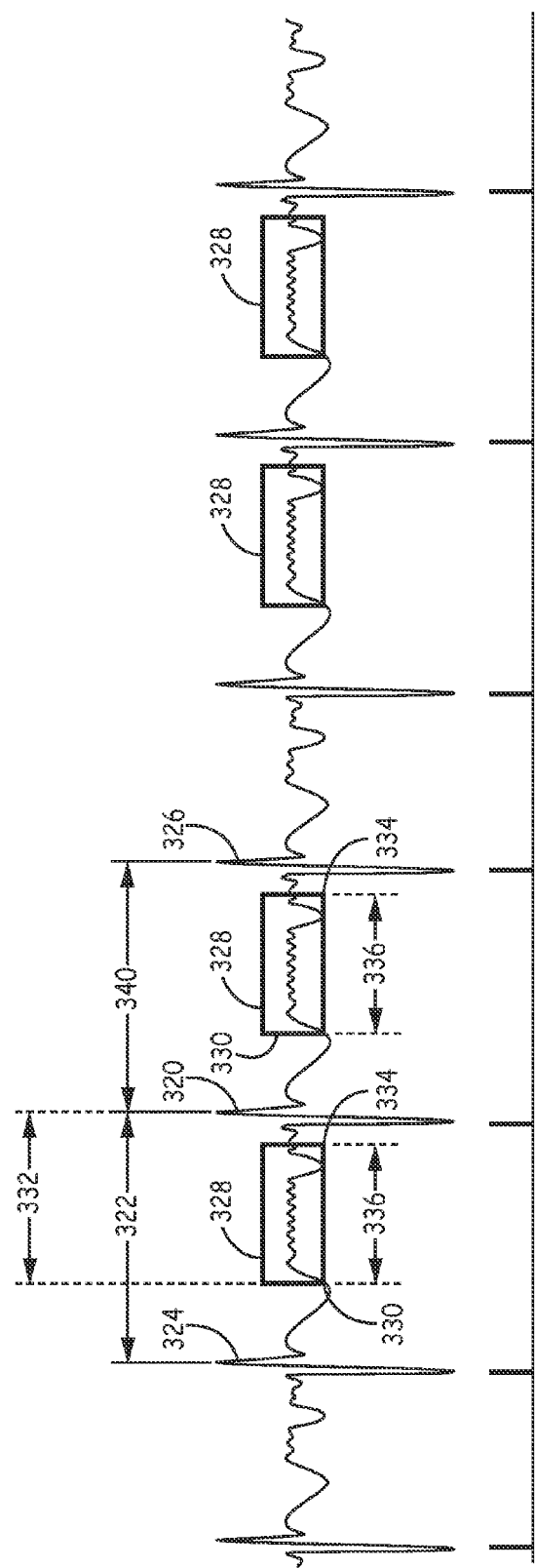
FIG. 7 is a schematic diagram of detecting an atrial arrhythmia according to an embodiment of the disclosure.

FIG. 7 is a schematic diagram of detecting an atrial arrhythmia according to an embodiment of the disclosure. As illustrated in FIGS. 4 and 5, in order to determine whether a sensed R-wave 320 satisfies the RR-interval parameters in Block 302, the device determines whether an RR interval 322 extending between the current R-wave 320 and a previous sensed R-wave 324 is greater than an interval threshold, such as 780 ms for example. If the RR interval 322 is not greater than the interval threshold, the RR-interval parameter is not satisfied, No in Block 302, and the process is repeated with the next RR interval 326. If the RR interval 322 is greater than the interval threshold, the RR interval parameter is satisfied, Yes in Block 302.

According to another embodiment, additional RR interval parameters may also be included in the determination as to whether the RR interval parameters have been satisfied in Block 302. For example, using R wave 326 as an example, in addition to the determination of whether the associated RR interval 340 satisfies the RR interval threshold, the device may also compare the RR interval 340 associated with the current R wave 326 with one or more previously determined RR intervals, such as interval 322 for example, and determine whether a relative change associated with the current RR-interval 340 is greater than a change threshold, such as 100 ms, for example. If the relative change associated with the current RR-interval is not greater than the change threshold, the RR interval parameter is not satisfied in Block 302. If the relative change associated with the current RR interval is greater than the change threshold, the RR-interval parameter is satisfied in Block 302.

In this way, if one of the RR intervals parameters are not satisfied, no P-wave window determination is made, and the process is repeated with the next R wave. If the RR interval parameter or one of the RR interval parameters are satisfied, the RR interval parameter is satisfied in Block 302, and the device determines a P wave window 328 associated with the R-wave 320 for determining whether the R wave 320 includes an associated P-wave. For example, in order to determine the P wave window 328, the device determines a P-wave window start point 330 located a predetermined distance 332 prior to the R-wave, such as 620 ms for example, and a P wave window endpoint 334 is located at a predetermined distance 336 subsequent to the P wave start point 330, such as 600 ms, for example, so that the P wave window 328 extends 600 ms between the P wave start point 330 and the P wave endpoint 334. Each time a P wave window 328 is determined, a P wave counter is updated by one, until the predetermined number of P wave windows are identified, such as four P wave windows, for example.

Figure 8:
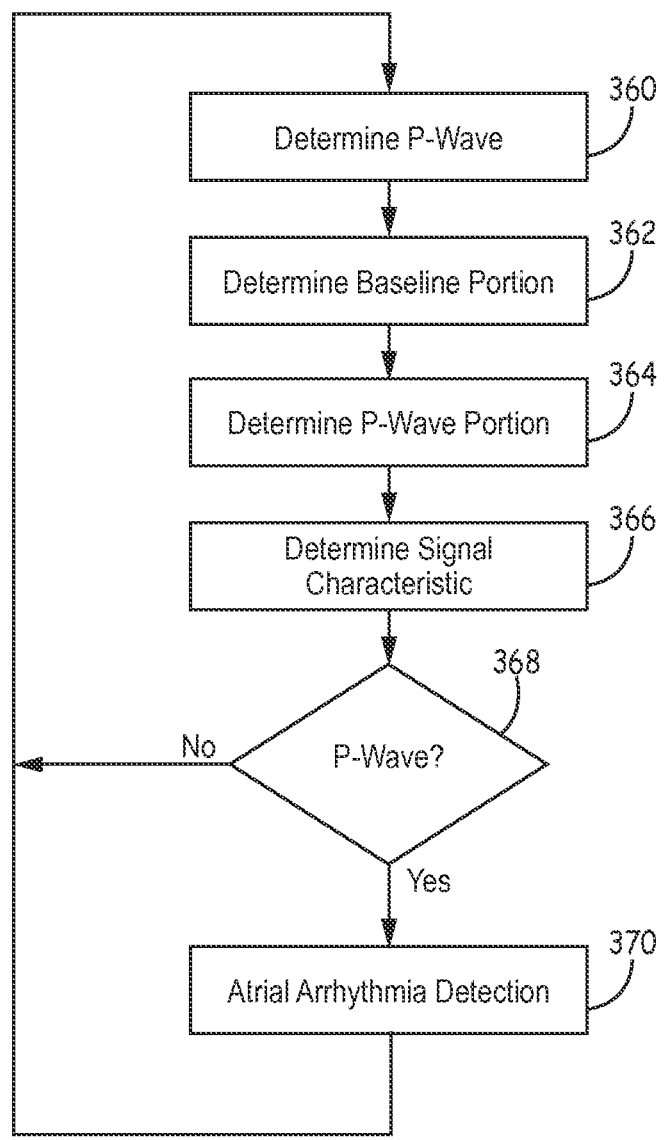
FIG. 8 is a flowchart of a method of detecting an atrial arrhythmia in a medical device according to an embodiment of the disclosure.

FIG. 8 is a flowchart of a method of detecting an atrial arrhythmia in a medical device according to an embodiment of the disclosure. In response to the predetermined number of P-waves being identified, No in Block 306 of FIG. 8, the device determines P-wave evidence for determining whether a P-wave is likely detected, Block 308, and utilizes the determined P-wave evidence to augment atrial arrhythmia detection, Block 310, described, for example, in commonly assigned U.S. patent application Ser. No. 14/695,111 to Sarkar et al., incorporated herein by reference in it's entirety. As illustrated in FIG. 8, during the determination of P-wave evidence, the device determines a characteristic P-wave in response to the current determined P-waves, Block 360. For example, according to one embodiment, the device determines an average P-wave from the four determined P-waves that is identified as the characteristic P-wave. The associated P-wave window is then divided into a baseline potion, Block 362, and a P-wave portion, Block 364, and determines signal characteristics, Block 366, for one or both of the baseline window and the P-wave window. A determination is then made, based on the determined signal characteristics, whether the characteristic P-wave is confirmed as being a P-wave, Block 368.

If the characteristic P-wave is not confirmed as being a P-wave, No in Block 368, the device waits for the next predetermined number of P-waves to be identified, Yes in Block 306 of FIG. 8, and the process, Blocks 360-368, is repeated using the next identified P-waves. If the characteristic P-wave is confirmed as being a P-wave, Yes in Block 368, the device utilizes the determination of a P-wave being present to augment atrial arrhythmia detection, Block 370, as described for example, in commonly assigned U.S. patent application Ser. No. 14/695,111 to Sarkar et al., incorporated herein by reference in it's entirety.

Figure 9:
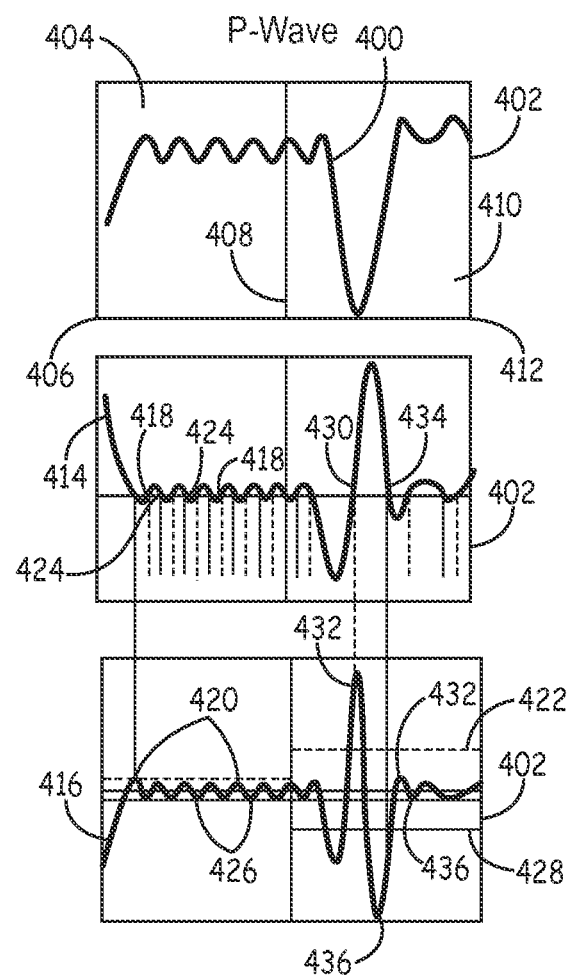
FIG. 9 is a schematic diagram of detecting an atrial arrhythmia in a medical device, according to an embodiment of the disclosure.

FIG. 9 is a schematic diagram of detecting an atrial arrhythmia in a medical device, according to an embodiment of the disclosure. As illustrated in FIGS. 8 and 9, in order to determine P-wave evidence (Block 308 of FIG. 6), the device determines a characteristic P-wave 400 having a characteristic P wave window 402 determined by averaging the determined four P-wave windows, as described above. The device divides the P-wave window 402 into a baseline portion 404, extending from the P-wave window start point 406 to a midpoint of the window 408, and a P-wave portion 410, extending from the midpoint of the window 408 to a P-wave window endpoint 412. The device determines a first derivative of the P-wave signal 414 and a second derivative of the p-wave signal 416, and determines corresponding second derivative values 420 associated with positive going zero crossings 418 of the first derivative signal 414 within the baseline portion 404 of the first derivative signal window 402. In one embodiment, the first derivative of the P wave signal can be computed as the difference between points separated by eight samples, and the second derivative can be computed as the difference between points separated by four sample in the first derivative.

The device determines the maximum amplitude of the second derivative values 420 associated with the positive going zero crossings 418, and the determined maximum amplitude value is then used to generate a first threshold 422 for evaluating the second derivative P-wave signal 416 within the P-wave portion 410 of the second derivative window 402. According to one embodiment, the threshold 422 is set as a multiple of the maximum of the second derivative values 420, such as twice the maximum of the second derivative values 420, for example.

In the same way, the device determines a corresponding second derivative value 426 for each negative going zero crossing 424 of the derivative signal 414 within the baseline portion 404 of the window 402. A minimum amplitude of the second derivative values 426 associated with the negative going first derivative zero crossings 424 is determined, and the determined minimum amplitude value is used to generate a second threshold 428 for evaluating the second derivative P-wave signal 416 within the P-wave portion 410 of the window 402. According to one embodiment, the threshold 428 is set as a multiple of the minimum of the second derivative values 426, such as twice the minimum of the second derivative values 426, for example.

Using the first threshold 422 determined in response to the determined maximum of the second derivative values 420, the device determines, for each positive going zero crossing 430 of the first derivative signal within the P-wave portion 410 of the first derivative window, a corresponding amplitude 432 of the second derivative signal within the P-wave portion 410 of the corresponding second derivative signal 416. The device compares the resulting maximum amplitudes 432 of the second derivative signal 416 signal within the P-wave portion 410 of the window 402 to the first threshold 422. Similarly, using the second threshold 422 determined in response to the determined minimum of the second derivative values 420, the device compares, for one or more negative going zero crossing 434 of the first derivative signal 414, the corresponding minimum amplitude 436 of the second derivative signal 416 signal within the P-wave portion 410 of the window 402 to the second threshold 428.

A P-wave is determined to have occurred, Yes in Block 368 of FIG. 8, if either the number of maximum amplitudes 432 determined to be greater than or equal to the first threshold 422 is equal to one, or the number of minimum amplitudes 432 determined to be less than or equal to the second threshold 428 is equal to one. If both the number of maximum amplitudes 432 determined to be greater than or equal to the first threshold 422 and the number of minimum amplitudes 432 determined to be less than or equal to the second threshold 428 is not equal to one, a P-wave is not determined to have occurred, No in Block 368 of FIG. 8. The result of the determination of whether a P-wave is identified is then used during the determination of an atrial arrhythmia event, as described for example, in commonly assigned U.S. patent application Ser. No. 14/695,111 to Sarkar et al., incorporated herein by reference in it's entirety.

As described above, during the arrhythmia detection scheme, the device initially determines whether to classify a rhythm as being either an atrial fibrillation event or as not being an atrial fibrillation event by determining the dispersion, or differences in patterns of RR intervals collected over a rhythm detection time interval, using a Lorentz scatter plot, for example. In order to reduce the number of false positives that occur during this initial determination of an atrial fibrillation event, the device augments the initial determination of atrial fibrillation by determining whether a P-wave occurs during the rhythm detection time intervals, as described above. If a P-wave is determined to occur, the initial determination that the cardiac signal sensed during the rhythm detection time interval was associated with an atrial fibrillation event for that rhythm detection time interval is identified as likely being a false determination of an atrial fibrillation episode, and therefore the device identifies the rhythm detection time interval as not being an atrial fibrillation event, as described above. On the other hand, if a P-wave is not determined to occur, the initial determination that the cardiac signal sensed during the rhythm detection time interval was associated with an atrial fibrillation event for that rhythm detection time interval is confirmed.

Figure 10:
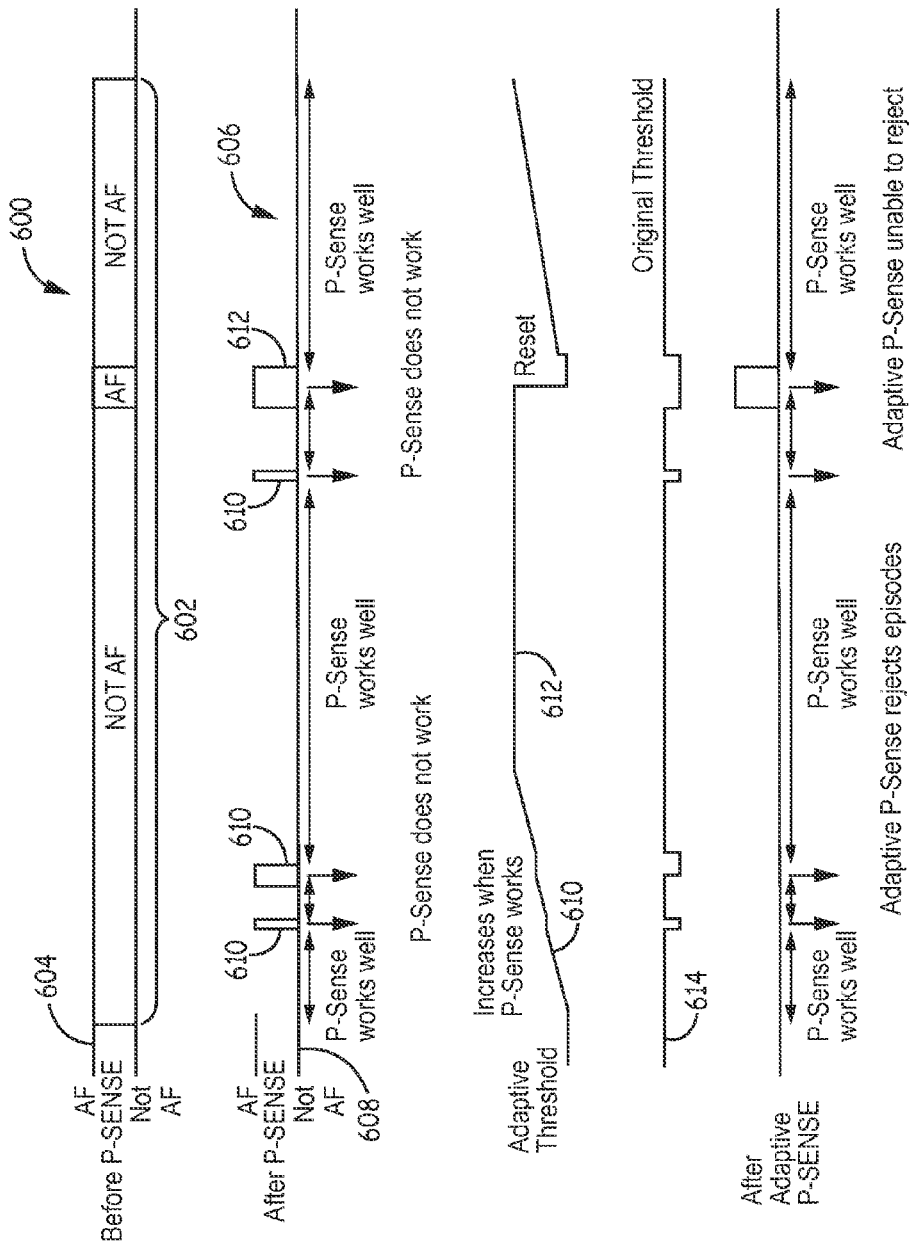
FIG. 10 is a schematic diagram of adjusting a threshold during arrhythmia detection in a cardiac medical device, according to an embodiment of the present disclosure.

FIG. 10 is a schematic diagram of adjusting a threshold during arrhythmia detection in a cardiac medical device, according to an embodiment of the present disclosure. As illustrated in FIG. 10, during the initial atrial fibrillation detection 600, in which the AF detection is determined based on RR interval variability, there may be a long duration 602 in some cases over which the device initially detects multiple successive rhythm detection time intervals as being associated with an atrial fibrillation event 604, but for which this initial determination of atrial fibrillation 600 is identified as not being an atrial fibrillation event 608 as a result of a P-wave being determined to occur during the P-sense detection 606, as described above, resulting in the long duration 602 of false positives occurring. However, the inventors have determined that during such long duration 602 of false positive atrial fibrillation 604, there may be instances 610, caused by factors such as noise or by changes in posture by the patient, where a P-wave is no longer detected during the P-sense detection 606, and therefore one or more rhythm detection time intervals are inappropriately detected as being associated with an atrial fibrillation event. At the same time, however, there may be instances 612 where there are one or more rhythm detection time intervals that are appropriately detected as being associated with an atrial fibrillation event during the P-sense detection 606, i.e., not caused by non-arrhythmic events such as noise or a change in patient posture. Therefore, the algorithm of the present disclosure, described below, is intended to distinguish, during a long duration 602 of false positive AF detections, the inappropriate instances 610 of determining atrial fibrillation events from appropriate instances 612 of determining atrial fibrillation events, and to reject the inappropriate instances 610.

Figure 11:
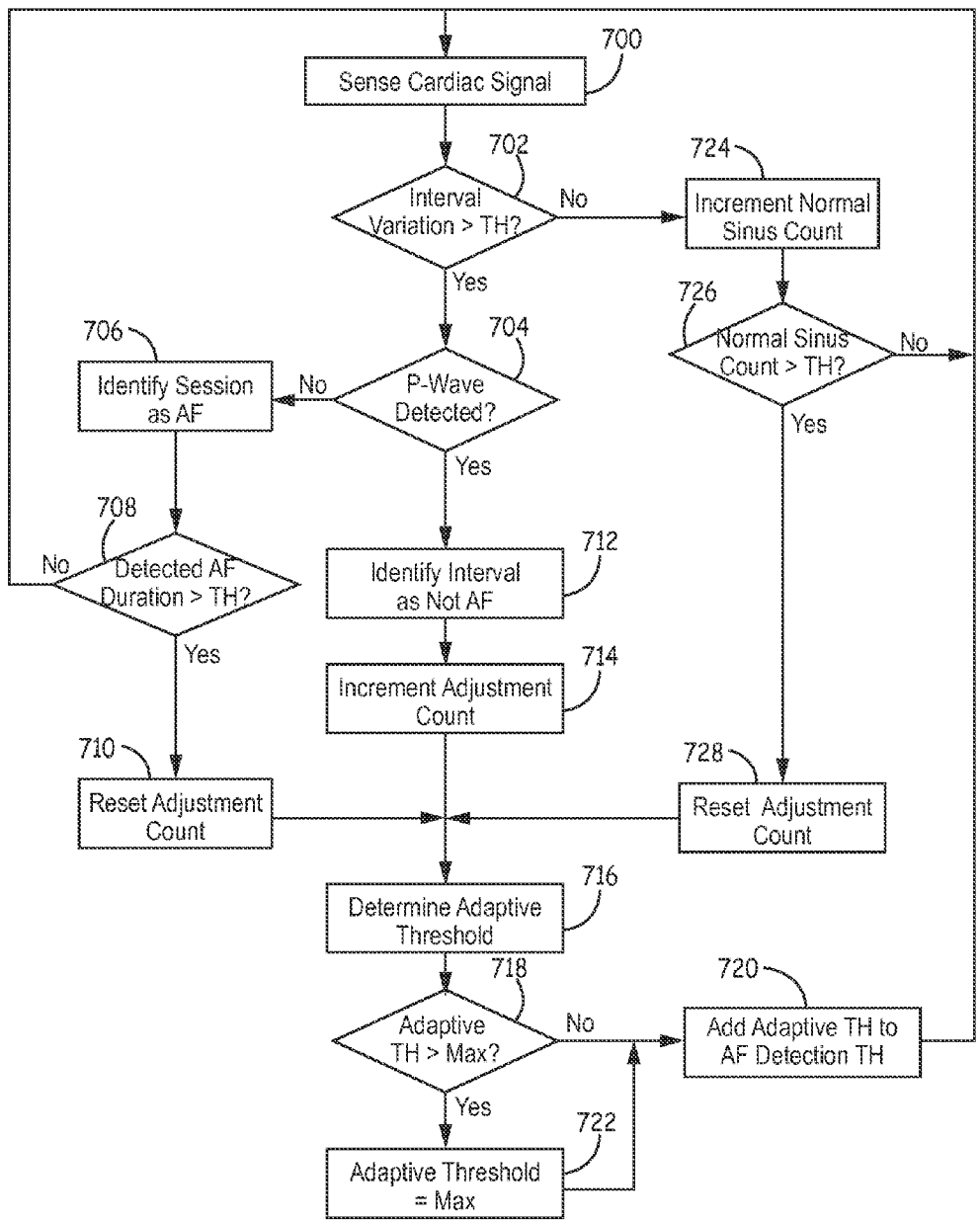
FIG. 11 is a flowchart of adjustment a threshold during arrhythmia detection in a cardiac medical device, according to an embodiment of the present disclosure.

FIG. 11 is a flowchart of adjustment of a threshold during arrhythmia detection in a cardiac medical device, according to an embodiment of the present disclosure. According to an embodiment of the present disclosure, in order to account for the inappropriate instances 610 of an atrial fibrillation event being identified during a long duration of initially detected AF episodes 602 that were determined as being false positives AF episodes based on P-wave information, the device 10 adaptively adjusts the AF detection threshold that is used during the initial determination of atrial fibrillation 600 in Block 224 of FIG. 5, described above. For example, as illustrated in FIGS. 10 and 11, during detection of atrial fibrillation events, the device senses a cardiac signal, Block 700, and performs the initial atrial fibrillation detection 600 by determining whether or not to classify a rhythm associated with the signal as being an atrial fibrillation event or as not being an atrial fibrillation event by determining the dispersion, or differences in patterns of RR intervals, for example, as described above.

In particular, the device determines, as described above, whether the interval variation as defined by the AF evidence score determined for the two minute interval is greater than the AF detection threshold, Block 702. If the interval variation is greater than the AF detection threshold, Yes in Block 702, the device performs the P-sense detection 606 by determining whether evidence of P-waves was found during the two-minute interval, Block 704. If evidence of P-waves is not identified, No in Block 704, the two minute interval session is identified as being an atrial fibrillation event, Block 706, and a determination is made as to whether a count of the number of consecutive atrial fibrillation detection intervals, i.e., two minute intervals, or the duration for which atrial fibrillation has been currently determined to be occurring, is greater than a detected AF duration threshold, Block 708.

As described above, the adaptive threshold feature of the present disclosure enables the device to reject instances 610 during a long duration 602 of false positives 604 where, because of factors such as noise or changes in posture by the patient, a P-wave is no longer detected during the P-sense detection 606, and therefore one or more rhythm detection time intervals are inappropriately detected as atrial fibrillation events during the P-sense detection 606. However, since there may be instances 612 where one or more rhythm detection time intervals are appropriately detected as atrial fibrillation events during the P-sense detection 606, i.e., the determination is not caused by non-arrhythmic events such as noise or a change in patient posture, and therefore these rhythm detection intervals are appropriately detected as atrial fibrillation events. Therefore, in order to distinguish the instances 610 that are inappropriately detected as being associated with an atrial fibrillation event from the instances 612 that are appropriately detected as being associated with an atrial fibrillation event, the AF duration threshold of Block 708 is set as a period of time for which the duration that atrial fibrillation is determined to be occurring is of a length most likely to be associated with an appropriately detected atrial fibrillation event, such as 12 minutes or six two minute intervals, for example.

If the count of the number of consecutive current atrial fibrillation detection intervals, or the duration for which atrial fibrillation has been currently determined to be occurring is greater than the detected AF duration threshold, Yes in Block 708, an adjustment count associated with the adjusting of the AF detection threshold, described below, is reset to zero, Block 710. On the other hand, if the count of the number of consecutive current atrial fibrillation detection intervals, or the duration for which atrial fibrillation has been currently determined to be occurring is not greater than the detected AF duration threshold, NO in Block 708, the process is repeated for the next two minute detection interval associated with the sensed cardiac signal, Block 700.

If a P-wave is identified during P-sense detection 606, Yes in Block 704, the detection interval is identified as not being associated with an atrial fibrillation event, Block 712, the adjustment count associated with the adjusting of the AF detection threshold, described below, is incremented, Block 714, and an adaptive threshold is determined, Block 716. According to an embodiment of the present invention, in order to determine the adaptive threshold, the device sets the adaptive threshold in Block 716 equal to a ratio of the adjustment count to a threshold tuning factor corresponding to a desired level of aggressiveness for rejecting an inappropriate instance 610 of AF determination during the P-sense detection 606. For example, the tuning factor may be set as 16 if a nominal level of aggressiveness is desired, 4 if an aggressive level is desired, or 8 if a level in between nominal and aggressive is desired.

Once the adaptive threshold is determined, Block 716, a determination is made as to whether the adaptive threshold is greater than a maximum adaptive adjustment threshold, Block 718. For example, according to one embodiment, the maximum adaptive threshold adjustment threshold may be set as 20, for example. If the adaptive threshold is not greater than the maximum adaptive adjustment threshold, No in Block 718, the adaptive threshold is added to the AF detection threshold, Block 720, and the process is repeated for the next AF detection interval associated with the sensed cardiac signal, Block 700, using the adjusted threshold. If the adaptive threshold is determined to be greater than the maximum adaptive adjustment threshold, Yes in Block 718, the adaptive threshold is not adjusted, i.e., remains equal to the maximum adaptive adjustment threshold, Block 722, and the maximum adaptive threshold is added to the AF detection threshold, Block 720, and the process is repeated for the next AF detection interval associated with the sensed cardiac signal, Block 700, using the adjusted threshold.

If it is determined during the initial detection 600 that the RR interval variation is not greater than the AF detection threshold, No in Block 702, the device increments a normal sinus count, Block 724, and determines whether the normal sinus count is greater than a normal sinus count threshold, Block 726. If the normal sinus count is not greater than a normal sinus count threshold, No in Block 726, the process is repeated for the next AF detection interval associated with the sensed cardiac signal, Block 700. According to the present disclosure, the normal sinus count corresponds to a count of or period of time during which the number of AF detection intervals, i.e., two minute intervals, for which either AF was not determined to be occurring during the initial determination for classifying the interval as AF or not AF, No in Block 224 of FIG. 5. If the interval variation in Block 702 is not greater than the threshold for a long period of time, six hours for example, then the algorithm determines that the chance for an appropriate detection due to interval variability is low and determines not to add the adaptive threshold to the AF detection threshold any longer, which is achieved by setting the adjustment count to zero, Block 728. If the normal sinus count is greater than a normal sinus count threshold, Yes in Block 726, the adjustment count associated with the adjusting of the AF detection threshold, described below, is reset to zero, Block 728, resulting in the adaptive threshold being adjusted to zero in Block 716 so that the AF detection threshold of Block 224 of FIG. 5 returns to it's initial, non-adjusted value.

In this way, during periods of P-sense detection 606 when atrial fibrillation is not being identified 608, Yes in Block 704, the adaptive threshold 612 is increased, Block 714, and added to the AF threshold 614, Block 720, until the adaptive threshold 610 reaches an adaptive threshold maximum 616, Yes in Block 718. If a P-wave is no longer identified during a detection interval, No in Block 704, and therefore atrial fibrillation is identified, Block 706, the device determines whether the duration for which atrial fibrillation has been currently determined to be occurring is greater than the detected AF duration threshold, Block 708. For example, the duration of instances 610 will not be greater than the detected AF duration threshold, and therefore the adaptive adjusting of the AF threshold 614 will continue. Once the duration is greater than the detected AF duration threshold, Yes in Block 708, such as in instance 612, or if the normal sinus count Block 724 is greater than the normal sinus count threshold, Yes in Block 726, indicating atrial fibrillation is no longer being inappropriately detected by the device, the adaptive threshold 612 is reset to zero, Blocks 710 and 728, respectively, so that the AF detection threshold of Block 224 of FIG. 5 returns to it's initial, non-adjusted value 614. By adaptively increasing the AF detection threshold 614 described in Block 224 of FIG. 5 during periods when initial atrial fibrillation detection 600 determinations of atrial fibrillation are identified as false positives, i.e., not atrial fibrillation 608, during the P-sense detection 606, instances 610, associated with noise or patient movement are rejected as being atrial fibrillation episodes. However, instance 612 where atrial fibrillation is detected, Block 706, during the long duration 602 that occur over a period time greater than the AF duration threshold, Yes in Block 708, the adaptive threshold 612 is reset to zero, Block 710, and therefore the AF detection threshold 614 is not increased and the AF episode is identified.

It is understood that while the method and apparatus for adjusting a threshold during atrial arrhythmia detection has been described in terms of identifying an atrial fibrillation event, it is understood that the present disclosure is not intended to be limited for using during determination if an atrial fibrillation event. For example, in addition to being utilized during the determination of atrial fibrillation, the method and apparatus for adjusting a threshold during atrial arrhythmia detection described above may be similarly utilized to update an atrial tachycardia detection threshold used to determine whether an atrial tachycardia event is occurring. As described above, the device determines whether a sensed cardiac signal is an atrial tachycardia event, and whether the cardiac signal contains a P-wave portion, the results of which are utilized to augment an atrial tachycardia determination process during long durations of false positives, as described above, so that an adaptive threshold may therefore also be generated during detection of atrial tachycardia, as described above.

Thus, an apparatus and method have been presented in the foregoing description with reference to specific embodiments. It is appreciated that various modifications to the referenced embodiments may be made without departing from the scope of the invention as set forth in the following claims.

We claim:

1. An implantable medical device for determining an atrial arrhythmia event, comprising:
    a cardiac sensing device comprising a housing having circuitry positioned therein;
    a plurality of electrodes electrically coupled to the circuitry to sense a cardiac signal; and
    a processor configured to generate an initial detection of an atrial arrhythmia event in response to an atrial arrhythmia threshold, determine whether a P-wave is detected during the initial detection, identify the initial detection as a false positive detection in response to a P-wave being detected, determine an adaptive threshold in response to the P-wave being detected, adjust the atrial arrhythmia threshold in response to the adaptive threshold, and generate a subsequent detection of an atrial arrhythmia event using the adjusted atrial arrhythmia threshold.

2. The implantable medical device of claim 1, wherein the atrial arrhythmia event comprises an atrial fibrillation event.

3. The implantable medical device of claim 1, wherein the processor is further configured to increment an adjustment count in response to the initial detection being identified as a false positive detection, and determine the adaptive threshold in response to the adjustment count.

4. The implantable medical device of claim 3, wherein the processor is further configured to set the adaptive threshold equal to a ratio of the adjustment count and a tuning factor corresponding to a desired level of aggressiveness for rejecting inappropriate determinations of the atrial arrhythmia event.

5. The implantable medical device of claim 3, wherein the processor is configured to determine whether the adaptive threshold is greater than a maximum adaptive threshold, and add the adaptive threshold to the atrial arrhythmia threshold in response to the adaptive threshold not being greater than the maximum adaptive threshold.

6. The implantable medical device of claim 5, wherein the processor is configured to set the adaptive threshold equal to the maximum adaptive threshold and add the maximum adaptive threshold to the atrial arrhythmia threshold in response to the adaptive threshold being greater than the maximum adaptive threshold.

7. The implantable medical device of claim 1, wherein the processor is configured to confirm the initial determination of the atrial arrhythmia event in response to a P-wave not being detected, determine whether a duration of the detected atrial arrhythmia event is greater than a duration threshold, and set the adjustment count to zero in response to the duration of the detected atrial arrhythmia event being greater than the duration threshold.

8. The implantable medical device of claim 7, wherein the processor is configured to determine an RR-interval variation associated with the sensed cardiac signal, determine an atrial arrhythmia score in response the RR-interval variation, determine whether the score is greater than the atrial arrhythmia threshold, increment a normal sinus count, determine whether the normal sinus count is greater than a normal sinus count threshold, and set the adjustment count to zero in response to the normal sinus count being greater than the normal sinus count threshold.

9. The implantable medical device of claim 8, wherein the processor is further configured to increment an adjustment count in response to the initial detection being identified as a false positive detection, and determine the adaptive threshold in response to the adjustment count.

10. The implantable medical device of claim 9, wherein the processor is further configured to set the adaptive threshold equal to a ratio of the adjustment count and a tuning factor corresponding to a desired level of aggressiveness for rejecting inappropriate determinations of the atrial arrhythmia event.

11. The implantable medical device of claim 10, wherein the processor is configured to determine whether the adaptive threshold is greater than a maximum adaptive threshold, and add the adaptive threshold to the atrial arrhythmia threshold in response to the adaptive threshold not being greater than the maximum adaptive threshold.

12. The implantable medical device of claim 11, wherein the processor is configured to set the adaptive threshold equal to the maximum adaptive threshold and add the maximum adaptive threshold to the atrial arrhythmia threshold in response to the adaptive threshold being greater than the maximum adaptive threshold.

13. The implantable medical device of claim 12, wherein the atrial arrhythmia event comprises an atrial fibrillation event.

14. The implantable medical device of claim 1, wherein the atrial arrhythmia event comprises an atrial tachycardia event.

15. A method of determining an atrial arrhythmia event in an implantable medical device, comprising:
sensing a cardiac signal;
generating an initial detection of an atrial arrhythmia event in response to an atrial arrhythmia threshold;
determining whether a P-wave is detected during the initial detection;
identifying the initial detection as a false positive detection in response to a P-wave being detected;
determining an adaptive threshold in response to the P-wave being detected;
adjusting the atrial arrhythmia threshold in response to the adaptive threshold; and
generating a subsequent detection of an atrial arrhythmia event using the adjusted atrial arrhythmia threshold.

16. The method of claim 15, wherein the atrial arrhythmia event comprises an atrial fibrillation event.

17. The method of claim 15, further comprising:
incrementing an adjustment count in response to the initial detection being identified as a false positive detection; and
determining the adaptive threshold in response to the adjustment count.

18. The method of claim 17, further comprising setting the adaptive threshold equal to a ratio of the adjustment count and a tuning factor corresponding to a desired level of aggressiveness for rejecting inappropriate determinations of the atrial arrhythmia event.

19. The method of claim 17, further comprising:
determining whether the adaptive threshold is greater than a maximum adaptive threshold; and
adding the adaptive threshold to the atrial arrhythmia threshold in response to the adaptive threshold not being greater than the maximum adaptive threshold.

20. The method of claim 19, further comprising:
setting the adaptive threshold equal to the maximum adaptive threshold; and
adding the maximum adaptive threshold to the atrial arrhythmia threshold in response to the adaptive threshold being greater than the maximum adaptive threshold.

21. The method of claim 15, further comprising:
confirming the initial determination of the atrial arrhythmia event in response to a P-wave not being detected;
determining whether a duration of the detected atrial arrhythmia event is greater than a duration threshold; and
setting the adjustment count to zero in response to the duration of the detected atrial arrhythmia event being greater than the duration threshold.

22. The method of claim 15, further comprising:
determining an RR-interval variation associated with the sensed cardiac signal;
determining an atrial arrhythmia score in response the RR-interval variation;
determining whether the score is greater than the atrial arrhythmia threshold;
incrementing a normal sinus count;
determining whether the normal sinus count is greater than a normal sinus count threshold; and
setting the adjustment count to zero in response to the normal sinus count being greater than the normal sinus count threshold.

23. The method of claim 22, further comprising:
incrementing an adjustment count in response to the initial detection being identified as a false positive detection; and
determining the adaptive threshold in response to the adjustment count.

24. The method of claim 23, further comprising setting the adaptive threshold equal to a ratio of the adjustment count and a tuning factor corresponding to a desired level of aggressiveness for rejecting inappropriate determinations of the atrial arrhythmia event.

25. The method of claim 24, further comprising:
determining whether the adaptive threshold is greater than a maximum adaptive threshold; and
adding the adaptive threshold to the atrial arrhythmia threshold in response to the adaptive threshold not being greater than the maximum adaptive threshold.

26. The method of claim 25, further comprising:
setting the adaptive threshold equal to the maximum adaptive threshold; and
adding the maximum adaptive threshold to the atrial arrhythmia threshold in response to the adaptive threshold being greater than the maximum adaptive threshold.

27. The method of claim 26, wherein the atrial arrhythmia event comprises an atrial fibrillation event.

28. The method of claim 15, wherein the atrial arrhythmia event comprises an atrial tachycardia event.

* * * * *